United States Patent
Kohl et al.

(10) Patent No.: US 6,818,178 B2
(45) Date of Patent: Nov. 16, 2004

(54) METHOD FOR HIGH VACUUM STERILIZATION OF CLOSURES

(75) Inventors: Nelson E. Kohl, Philadelphia, PA (US); Richard J. Falkowski, Folsom, PA (US)

(73) Assignee: Environmental Tectonics Corporation, Southampton, PA (US)

( * ) Notice: Subject to any disclaimer, the term of this patent is extended or adjusted under 35 U.S.C. 154(b) by 167 days.

(21) Appl. No.: 10/208,800

(22) Filed: Aug. 1, 2002

(65) Prior Publication Data

US 2003/0035753 A1 Feb. 20, 2003

Related U.S. Application Data

(60) Provisional application No. 60/312,399, filed on Aug. 16, 2001.

(51) Int. Cl.[7] .............................. A61L 2/08; A61L 2/00; G01N 21/00; A45B 11/00; E04H 15/36
(52) U.S. Cl. ................................ 422/26; 422/1; 422/3; 422/28; 422/62; 422/108; 422/105; 422/295; 134/21; 134/25.1; 134/30; 134/84; 134/102.3; 134/133; 134/61
(58) Field of Search ...................... 422/3, 26, 111–112, 422/116, 62

(56) References Cited

U.S. PATENT DOCUMENTS

| | | | | |
|---|---|---|---|---|
| 4,309,381 A | * | 1/1982 | Chamberlain et al. | 422/3 |
| 4,497,773 A | * | 2/1985 | Kuelzow et al. | 422/26 |
| 4,759,909 A | * | 7/1988 | Joslyn | 422/26 |
| 5,238,660 A | * | 8/1993 | Dietwart | 422/295 |
| 5,439,655 A | * | 8/1995 | Fedegari | 422/297 |

* cited by examiner

*Primary Examiner*—Robert J. Warden, Sr.
*Assistant Examiner*—Monzer R. Chorbaji
(74) *Attorney, Agent, or Firm*—Gregory J. Gore

(57) ABSTRACT

A heat sterilization process for small, washed, and bagged articles such as vial stoppers includes a conditioning or air removal phase prior to sterilization. During the air removal phase, a substantial majority of the liquid moisture is removed from the bagged articles by introducing brief periods of dry, warm air to the autoclave chamber. The air is introduced in short bursts at the point of greatest vacuum while pressure pulsing the chamber during the air removal phase. The air is heated and injected into the chamber through a supply valve which is rapidly opened and closed while the chamber is maintained within a preselected vacuum range between the pressure pulses. The result is a greatly reduced time for a complete sterilization and drying process.

10 Claims, 6 Drawing Sheets

METHOD FOR HIGH VACUUM STERILIZATION OF CLOSURES

The present application is related to provisional patent application Ser. No. 60/312,399 entitled "Method for High Vacuum Sterilization Closures" filed on Aug. 16, 2001, priority from which is hereby claimed.

FIELD OF THE INVENTION

This invention relates generally to high vacuum steam sterilization processes which heat sterilize articles such as medical container closures. More specifically, it relates to the sterilization of bagged closures such as vial stoppers and caps used in the pharmaceutical industry.

BACKGROUND OF THE INVENTION

In order to accomplish the removal or destruction of all living organisms from objects, high vacuum steam sterilization provides an effective infection and contamination control in pharmaceutical environments. Sterilizers of this type safely and efficiently accomplish sterilization by utilizing saturated steam as the sterilant. The saturated steam is a gas and is therefore able to circulate by convection which allows the steam to penetrate porous objects in the sterilizer. This permits the efficient sterilization of a quantity of small parts which are delivered for sterilization in permeable bags. Small container closures such as elastomeric stoppers are used in high volume by the pharmaceutical industry and the efficient sterilization of these items is required. These parts are sealed in bags having a permeable membrane and are delivered packaged this way to a steam autoclave for sterilization. By way of example, the sterilizable bags may be of the type sold under the name Steribag™ by the West Company of Lionville, Pa.

A problem exists however because the bagged stoppers are sealed in the bags directly after washing without being dried. Thus, the stoppers are still wet from washing and therefore the bags contain a significant amount of water. Hence, the stoppers need to be dried as well as sterilized before they can be delivered to installation equipment which applies the stoppers to individual containers such as serum vials which hold the pharmaceutical products.

To sterilize bagged items such as the pharmaceutical closures which are the specific subject of the present invention, a vacuum autoclave must be used because air trapped in the bag must first be removed since it inhibits the process of steam sterilization. To achieve air removal, a vacuum steam autoclave typically subjects its contents to a conditioning or prevacuum phase in which the autoclave environment undergoes a series of alternating vacuum and steam cycles to remove air from the autoclave and the interior of the stopper bags. Three or four pulses are usually employed, each drawing a vacuum on the autoclave chamber and then introducing steam until the chamber reaches a predetermined positive pressure when the admission of steam is stopped and a vacuum is once again drawn. This type of pulsing is known to provide the greatest efficiency in quickly effecting the desired removal of air prior to sterilization. As described above, however, this conditioning process can actually add water to the interior of the sterilizable bags which adversely affects the duration of the drying cycle after sterilization.

Drying is normally accomplished by simple hot air convection at the end of the sterilization process. However, the steam sterilization process can be problematic to the drying cycle of bagged items because the steam can add water to the bag of stoppers if there is condensation of the steam. This further increases the drying time after sterilization which can take as long as eight hours for the total sterilization/drying process. Simply increasing the heat to speed the drying process is not a viable solution because the dry heat can be destructive to the elastomeric stoppers causing a deterioration in their elastomeric tensile strength, elongation, and durometer hardness.

Prior art patents of which the applicant is aware include U.S. Pat. No. 4,309,381 issued to Chamberlain et al. which discloses methods for establishing and ascertaining air removal in steam sterilization, however there are no teachings which address the problem or propose a solution to removing water content from small bagged articles. U.S. Pat. No. 4,759,909 issued to Joslyn discloses the use of air removal by subjecting the goods to a plurality of pressure pulses at above atmospheric pressure by alternate pressurization and venting of the chamber to atmospheric pressure during which air is removed from the chamber with steam prior to pressurized sterilization. There is, however, no teaching of admitting air during the pressure pulses while drawing a vacuum on the chamber during the air removal phase. The Joslyn patent does not address the problem of removal of water from materials or the problem of water content in sterilization bags of bagged articles. There is therefore a need in the art to accomplish the combined sterilization/drying process for bagged pharmaceutical closures more quickly and without having a destructive effect on the performance of the closures.

SUMMARY OF THE INVENTION

According to the present invention, a sterilization process for bagged articles as will be described more specifically with regard to the description of the preferred embodiment, a novel approach is taken with regard to the conditioning or air removal phase prior to sterilization. This has shown to not only prevent the addition of water to the sterilizable bags during this phase but in fact to remove 90 percent of the liquid moisture. This is accomplished by introducing brief periods of dry warm air to the autoclave chamber at the point of greatest vacuum during the prevacuum pulsing. It is contrary to logic to introduce air during the air removal phase when the objective is to remove air, however this method has shown surprising and unexpected results. While it is not fully understood why the present system works so effectively, it is believed that this timed admission of warm air during the conditioning pulse cycles maintains the temperature of the stoppers above their condensation point and also increases the mass of vapor flowing through the vacuum pump with the purging air being used as the transport medium for the condensable vapor. Thus, the liquid water in the product bags becomes greatly reduced.

More specifically, the applicant has invented a method of conditioning and sterilizing materials such as bagged vial stoppers comprising the steps of first placing the materials into a sealed vacuum steam autoclave chamber and then removing air from the chamber during an air removal phase by admitting steam into the chamber and initiating a series of vacuum pulses by a vacuum pump. The pulses include successive pressure-down and pressure-up segments between which air is injected into the chamber for a brief period while the chamber is maintained at below atmospheric pressure by the vacuum pump. The air is injected into the chamber through an air supply valve which is rapidly opened and closed to supply short bursts of air into the chamber while the chamber is maintained within a pre-selected pressure range between the successive pressure-down and pressure-up segments. The injected air is preferably heated and dried prior to being supplied into the chamber. After the air removal phase is complete, the materials are sterilized by introducing steam into the chamber for a period of time sufficient to effect sterilization. The step of sterilization is followed by a drying step where the bagged vial stoppers are dried with hot air while the chamber is held below atmospheric pressure.

The invention will be more clearly understood by those of skill in the art from the following drawings and description of the preferred embodiment. While the present invention will be described with reference to a specific embodiment, the description is illustrative of the invention and is not to be considered as limiting the invention. Various modifications to the invention can be made to the preferred embodiment by those skilled in the art without departing from the true spirit and scope of the invention as defined by the appended claims.

DESCRIPTION OF THE PREFERRED EMBODIMENT

Figure 5:
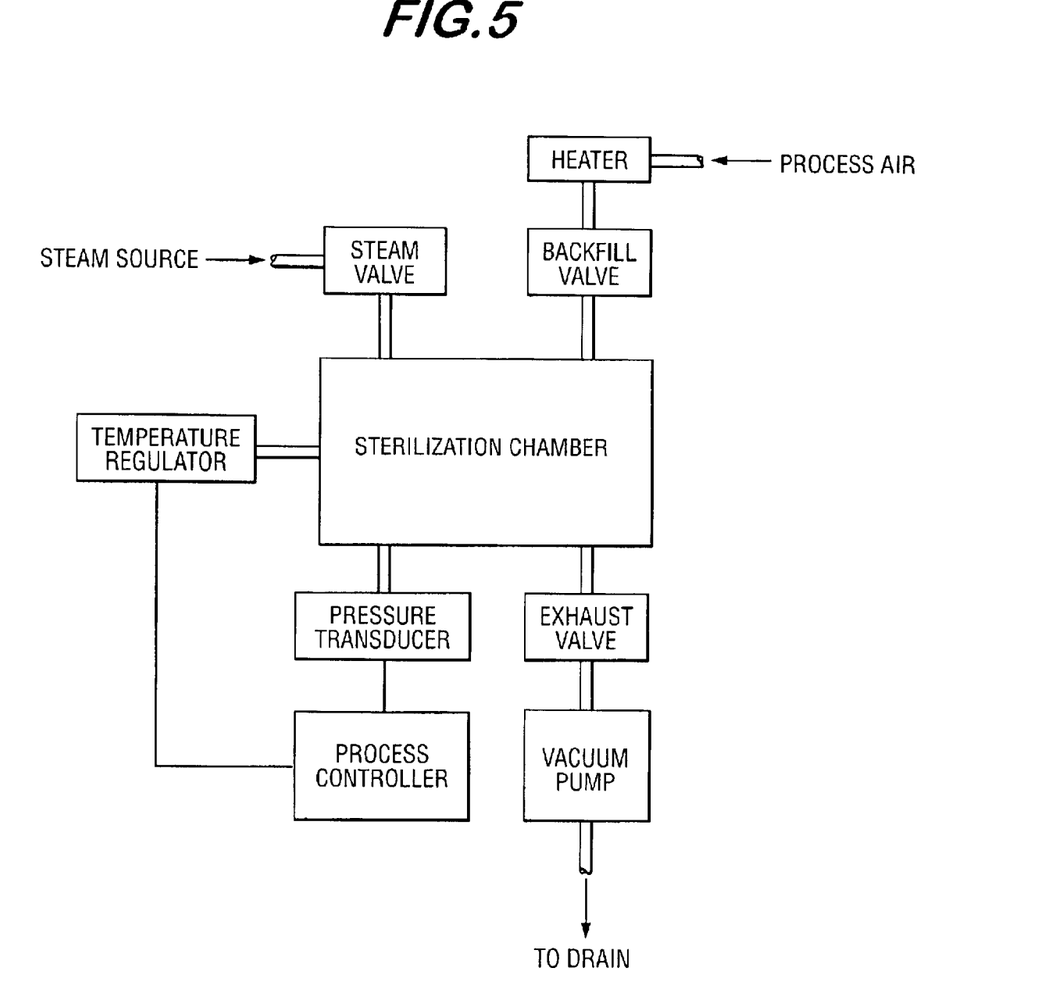
FIG. 5 is a diagram illustrating the basic components of the sterilizer utilized according to the inventive process.
Figure 6:
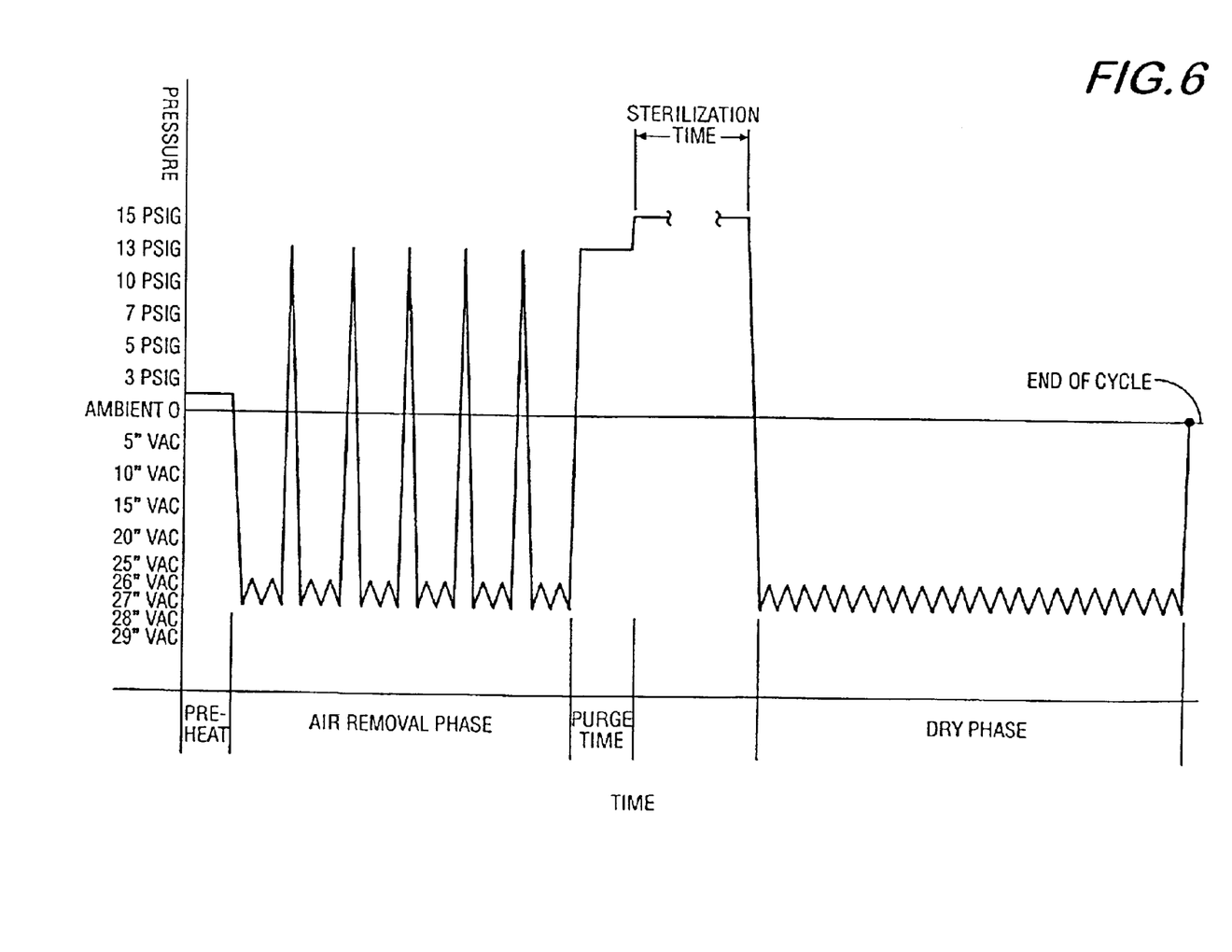
FIG. 6 is a pressure/time graph of the sterilizer environment utilizing the process of the invention.

The best mode of carrying out the invention will now be described with regard to the drawing FIGS. 1-6. FIGS. 1-4 are flowcharts of the inventive process. FIG. 5 shows the basic components of a vacuum steam autoclave used in accordance with the present inventive method. It will be understood that the FIG. 5 diagram is made for purposes of illustration only and that other associated devices are necessary for a complete operating system, however additional detail will not be necessary for those of ordinary skill in the art to fully comprehend and utilize the invention. It will be understood, for example, that the various valves and process control mechanisms are electromechanical devices which may be operated by a programmable controller which is electrically connected to each device and to appropriate sensors and a timer to achieve the regulated process as will be further described herein. FIG. 6 is a pressure/time graph that is exemplary of an actual test performed utilizing the best mode of the invention that will now be described.

The present invention resides in the steps of sterilization methodology which are carried out in general phases by operation of a process controller and appropriate sterilizer components as diagrammatically depicted in FIG. 5. Most of the various phases are timed events that may be controlled by any suitable control such as an Allen Bradley PLC. The overall process generally includes the following phases of a complete sterilization cycle: a preheat phase, an air removal phase, a sterilization phase, a drying phase, and finally an air inbleed phase.

Figure 1:
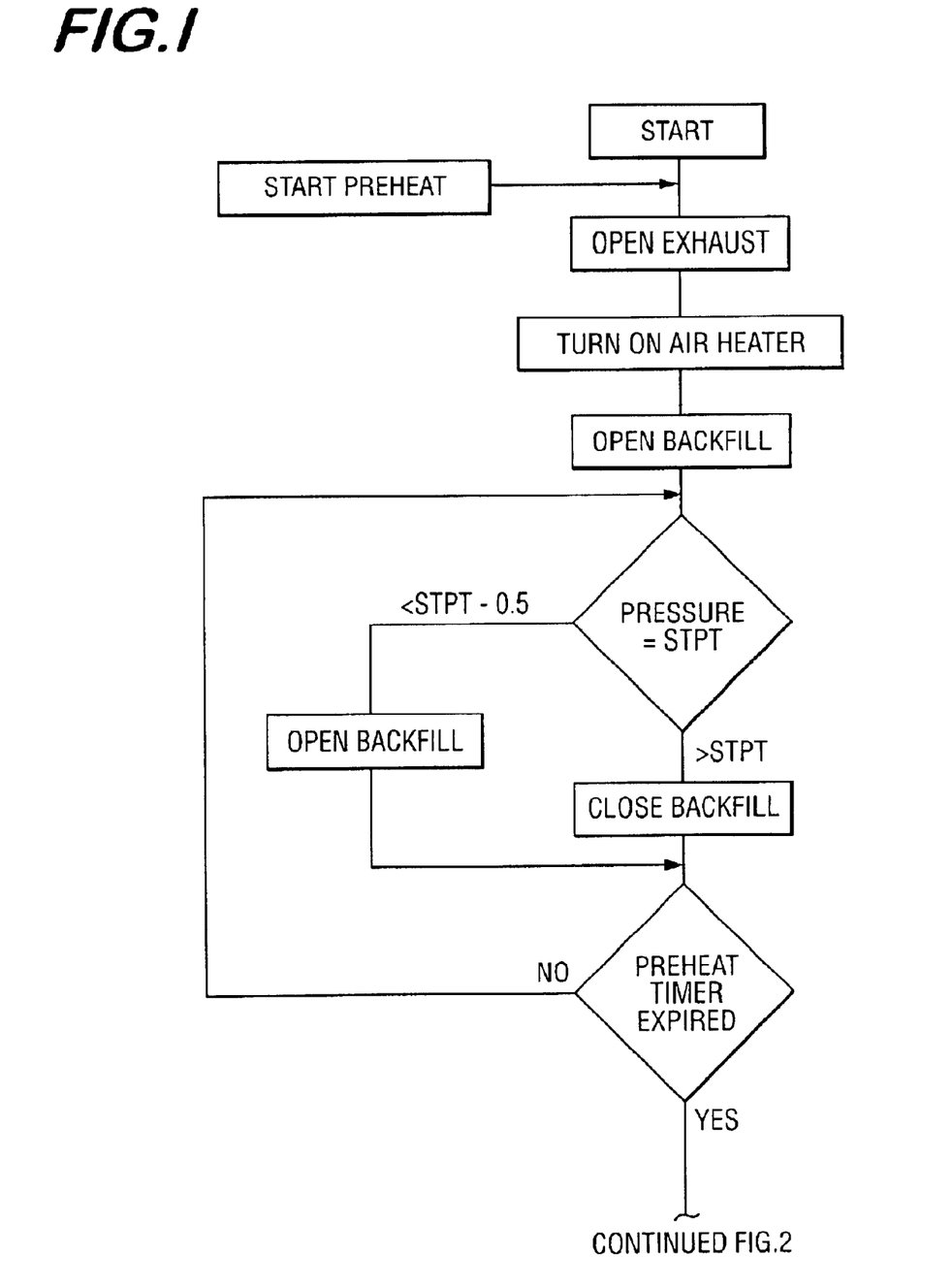
FIGS. 1-4 are process flowcharts which depict the various phases of the inventive process.

Referring now to FIG. 1, the first step is a preheat phase. To begin the preheat phase, a preheat phase timer is started while filtered process air is heated in the process air heating heat exchanger and delivered to the sterilization chamber through the backfill valve. During this period the chamber exhaust valve remains open and the chamber backfill valve opens and closes to maintain the proper setpoint (STPT) pressure in the chamber. This will continue until the preheat timer expires. The preheat phase is used to raise the temperature of the stopper load to assist water and air removal prior to sterilization. After the preheat timer elapses the controller advances the process to the air removal phase.

Figure 2:
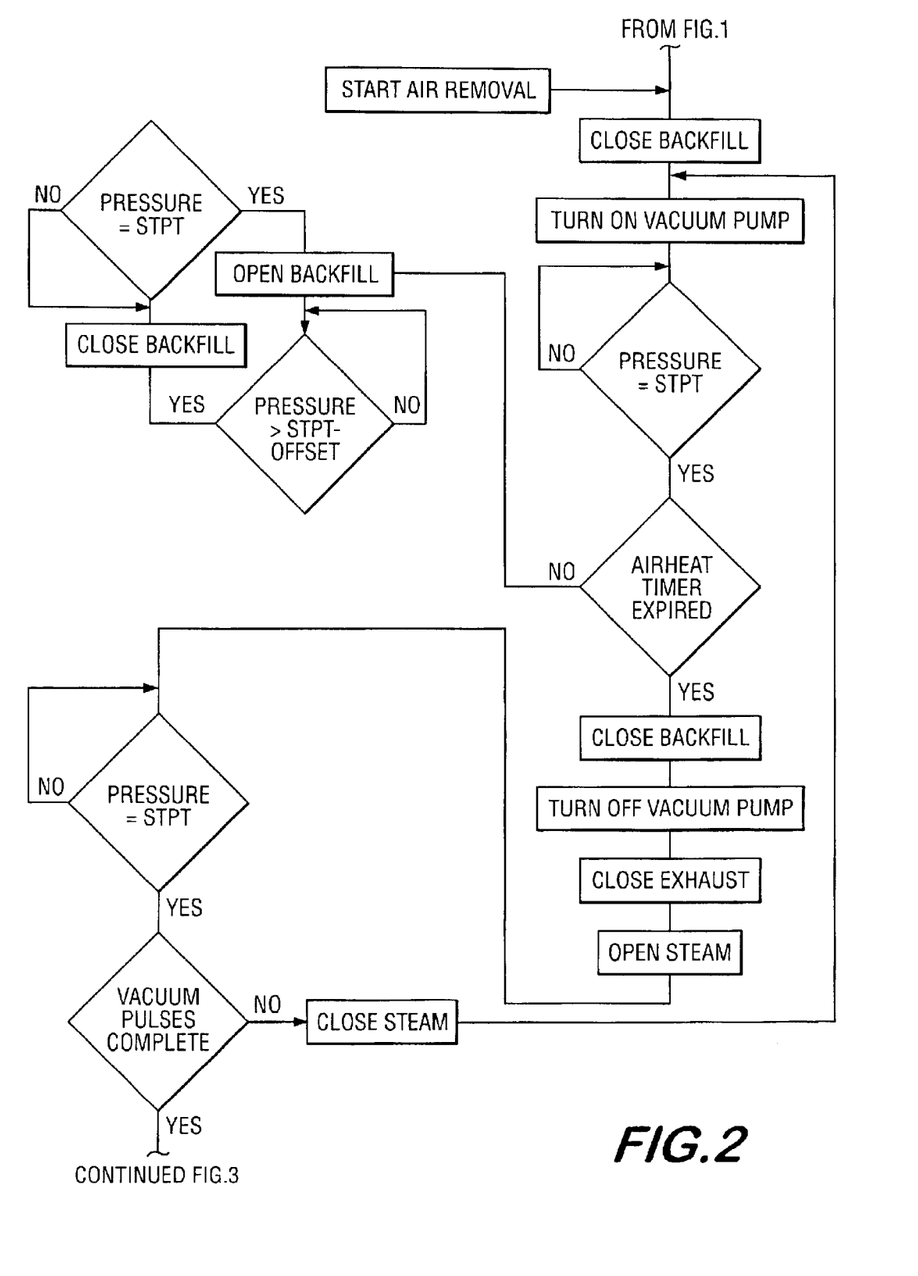

As shown in FIG. 2, the air removal phase begins with a series of vacuum pulses, each pulse cycle including a pressure "down" and a pressure "up" segment. The controller begins the first pulse with a pressure-down segment. During each pressure-down segment, the chamber backfill valve is shut off and the vacuum pump is turned on to allow a vacuum to be drawn on the chamber through the chamber exhaust valve. At the point of each pulse pressure-down segment when a programmed maximum vacuum pressure level is reached, a short timed period of heated air injection begins. During this period, bursts of heated air are supplied to the chamber from filtered process air which is heated in the process air heating heat exchanger and delivered to the chamber through the chamber backfill valve. This occurs as the vacuum pump continues to run to allow a vacuum to be drawn on the chamber through the open chamber exhaust valve while the chamber backfill valve opens and closes to maintain a prescribed vacuum level in the chamber. This provides the chamber with bursts of heated air during a brief period of maximum vacuum between down and up segments.

As further shown in FIG. 2, this extends the duration of each pulse at the point of maximum vacuum. The air injection feature of the process adds heated air to the stopper load so that more water vapor may be removed before the unit moves to the sterilize phase of the cycle. This is a key feature of the invention which is responsible for its dramatic results in greatly reducing the overall process time. Each period of hot air injection is followed by an up segment of each pulse during which the vacuum pump, chamber backfill valve, and chamber exhaust valve are shut off and steam is admitted into the chamber until the pressure reaches a programmed upper pressure limit. These up and down segments are alternatingly repeated until a programmed number of air removal pulses are completed at which point the controller starts a gravity purge portion of the air removal phase.

Figure 3:
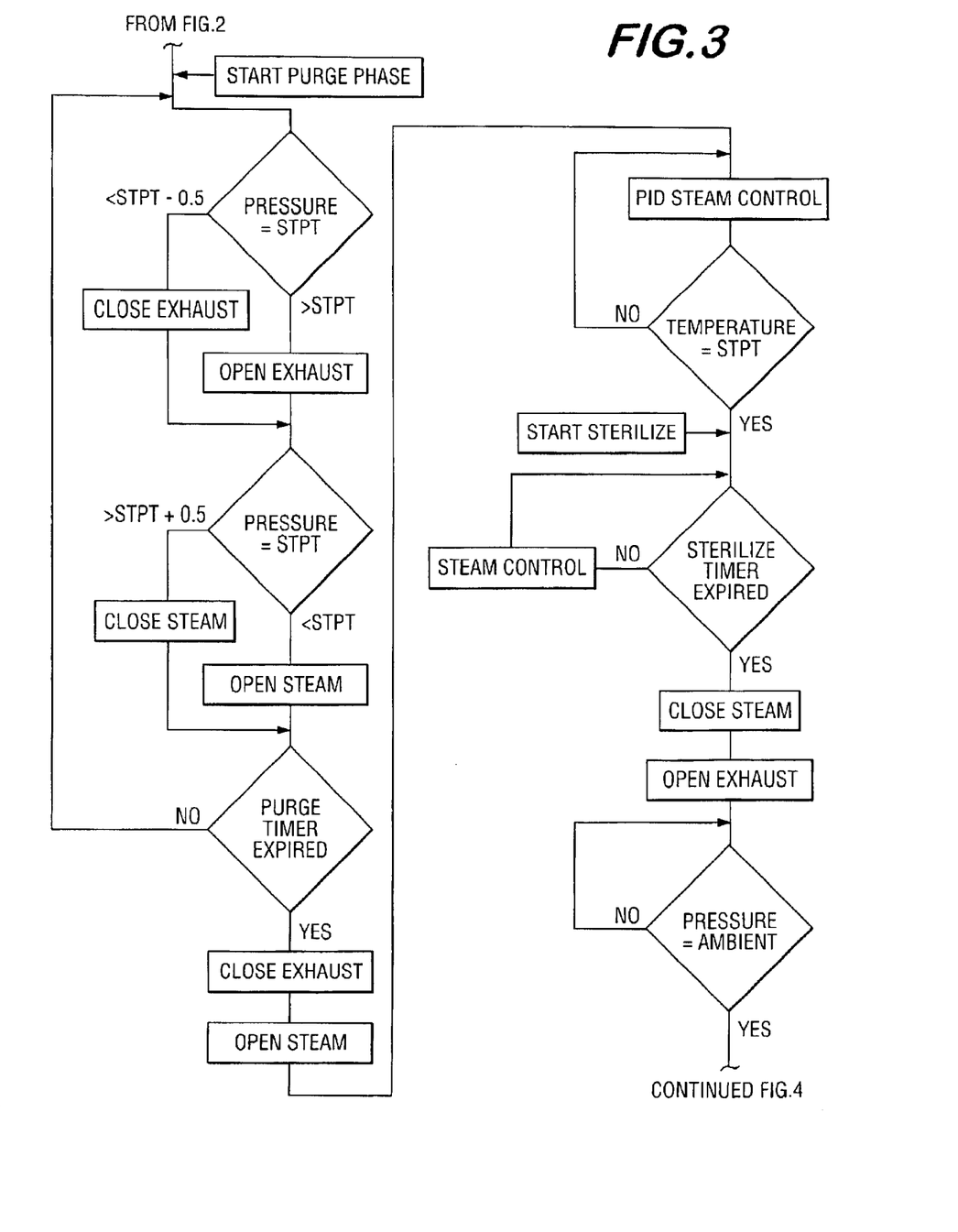

Referring now to FIG. 3, the gravity purge begins with a purge segment followed by a purge duration. During the purge segment, the chamber exhaust valve is closed while steam is admitted into the chamber through the chamber steam valve. Once the chamber reaches a programmed purge pressure, a purge timer is initiated and the chamber exhaust valve and the chamber steam valve modulate to maintain the chamber at the programmed purge pressure until the purge timer elapses. This completes the air removal phase.

When the air removal phase has been completed, the controller advances the process to the sterilization phase which, as further shown in FIG. 3, begins with closing the chamber exhaust valve and admitting steam to the chamber through the chamber steam valve. When the chamber reaches a temperature setpoint, a sterilize phase timer is started by the controller. Steam will continue to be admitted into the chamber through the chamber steam valve in a regulated manner to maintain a pre-determined chamber temperature. Once the sterilize phase timer has expired, the controller will then advance the process to a fast exhaust segment of this phase during which the chamber exhaust valve is opened to allow steam to be quickly vented out of the chamber. The chamber pressure will descend until ambient pressure is reached, when the controller advances the process to the drying phase.

Figure 4:
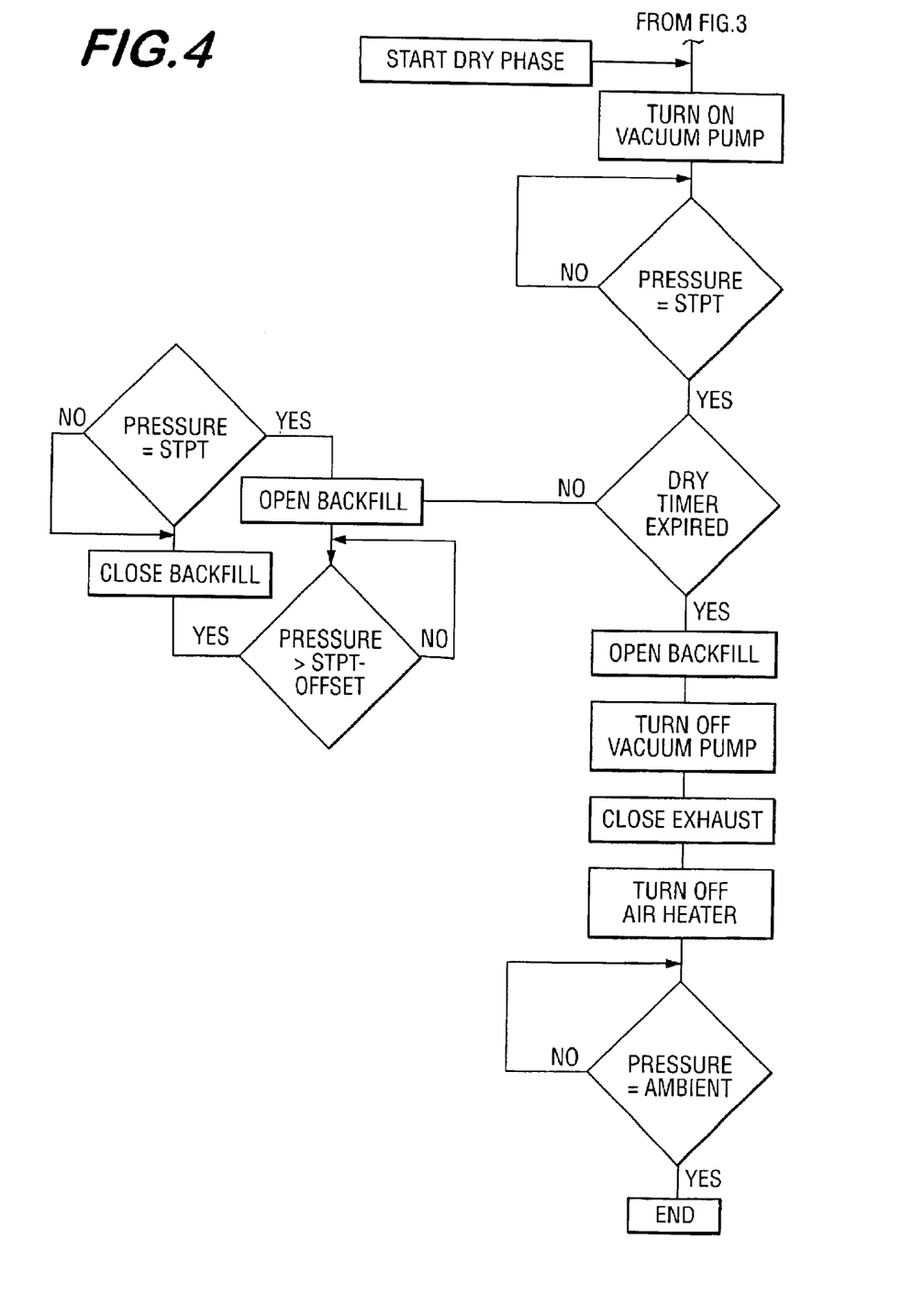

Referring now to FIG. 4, the drying phase is divided into two parts. During the first part, the controller turns on the vacuum pump and keeps the chamber exhaust valve open to allow a vacuum to be drawn on the chamber through the exhaust valve. Once a programmed drying vacuum level is reached, a second timed part of the drying phase begins by admitting heated, dry air through the backfill valve as the vacuum pump continues to run. A programmed drying vacuum level is maintained by the chamber backfill valve which opens and closes to offset the chamber vacuum by supplying air. This alternating air/vacuum pulsing is employed to remove more water from the stopper load. Pulsing will continue until the air drying timer expires.

When the air drying timer elapses, the controller shuts off the vacuum pump and advances the process to the air inbleed phase. During the air inbleed phase, heated process air enters the chamber through the chamber backfill valve until ambient pressure is attained at which point the process is ended.

Test Conditions and Results

FIG. 6 depicts a specific test of the above-described sterilization and drying method. This test was carried out on a high vacuum steam sterilizer produced by Environmental Tectonics Corporation of Southampton, Pa. The sterilizer had 196 cubic feet capacity, which for the purpose of this test received two loading carts, each containing 60 bags of vial caps. Each bag contained approximately 6.5 pounds of product including the weight of the liquid moisture in the bag. The specific procedures, tester's notes, and observed results of this test are as follows.

PREHEAT PHASE—Hot air cycles were begun for 10 minutes between 0.5 and 1.0 PSIG. After 10 minutes, advanced process to air removal phase.

AIR REMOVAL PHASE—Began (6) pre-vac pulses to 27" Hg. Upon first reaching 27" Hg., hot air cycles were begun for 2 minutes between 25" Hg. and 27" Hg. After 2 minutes timed out, charged chamber to 13 PSIG. When 13 PSIG was reached, went back to vacuum and started over. At the end of 6 prevacs, advanced to purge at 13 PSIG for 5 minutes. During the purge, utilized on-off steam purges through the unit to maintain 13 PSIG.

STERILIZE PHASE—After purge, advanced to sterilize and charged with steam to 122.7° C. and approximately 16.5 PSI. Held for sterilization time of 100 minutes. After sterilization, began fast exhaust to ambient.

DRY PHASE—Started a 45-minute drying phase. At a vacuum of 28" Hg. hot air was introduced until 26" Hg. was reached then vacuum back to 28" Hg. This phase was continued for 45 minutes.

AIR INBLEED PHASE—After 45-minute drying time, air inbleed with hot air was begun until ambient pressure was reached.

OBSERVED RESULTS—At the end of the process, product was sterile and contained no visible signs of moisture. All product was dry and ready for use.

Total Cycle Time using 100 minutes for sterilizing was approximately 240 minutes.

As will be readily apparent to those of skill in the art from the above description, the test results of the present invention achieve a sterilization/drying process for bagged closures for pharmaceutical use that require less than one half of the usual time. Thus, the objects of the invention to achieve a more efficient means of sterilization and drying bagged products without adversely affecting performance of the products have been achieved. There are other advantages and applications of the present invention and other types of products that require an advanced drying time that will benefit from the foregoing description of the invention. These other applications, adaptations, and modifications to what has been disclosed are to be considered within the scope and spirit of the invention although it has been disclosed only with regard to sterilization of products in the pharmaceutical industry. Therefore, the scope of the invention should not be limited to the specific preferred embodiment of the invention described herein but rather should be defined only by the following claims and their legal equivalents.

What is claimed is:

1. A method of conditioning and sterilizing materials, comprising the steps of:

placing materials into a sealed vacuum steam autoclave chamber;

removing air from the chamber during an air removal phase by admitting steam into the chamber and initiating a series of vacuum pulses by vacuum pump means, said pulses including successive pressure-down and pressure-up segments;

injecting heated air into the chamber during said air removal phase between said pulses after each pressure-down segment and before the next pressure-up segment; and sterilizing the materials by introducing steam into the chamber for a period of time sufficient to effect sterilization of the materials.

2. The sterilization method of claim 1 wherein the step of injecting air into the chamber during the air removal phase occurs while the chamber is maintained at below atmospheric pressure by said vacuum pump means.

3. The sterilization method of claim 2 wherein said air is injected into the chamber through an air supply valve which is rapidly opened and closed to supply short bursts of air into the chamber while the chamber is maintained within a pre-selected pressure range between said successive pressure-down and pressure-up segments.

4. The sterilization method of claim 3 including the additional step of heating and drying said air before injecting it into the chamber.

5. The sterilization process of claim 4 wherein said step of injecting air into the chamber occurs for a brief period between pressure pulses.

6. The sterilization method of claim 5 wherein said step of injecting air into the chamber occurs between pulses for approximately two minutes.

7. The sterilization method of claim 6 wherein said step of injecting air into the chamber occurs while the chamber is held in a vacuum range of between 25 and 27 inches of mercury.

8. The sterilization method of claim 1 wherein said step of sterilizing the materials is followed by the step of drying the materials with hot air in a vacuum.

9. The sterilization method of claim 1 wherein said period of time sufficient to effect sterilization is approximately 100 minutes.

10. The method of sterilizing and drying vial stoppers, comprising:

placing a plurality of vial stoppers into a semi-permeable bag while the stoppers are still wet from washing;

placing said bagged vial stoppers into a sealed vacuum steam autoclave chamber;

removing air from the chamber during an air removal phase by admitting steam into the chamber and initi ating a series of vacuum pulses by vacuum pump means, said pulses including successive pressure-down and pressure-up segments;

injecting air into the chamber during said air removal phase between said pulses after each pressure-down segment and before the next pressure-up segment by admitting air through a supply valve which is rapidly opened and closed supplying short bursts of air into the chamber; and sterilizing the materials by introducing steam into the chamber for a period of time sufficient to effect sterilization of the materials.

* * * * *